US011987600B2

(12) United States Patent
Lishko et al.

(10) Patent No.: US 11,987,600 B2
(45) Date of Patent: May 21, 2024

(54) CONTRACEPTIVE USE OF TRITERPENOIDS

(71) Applicant: The Regents of the University of California, Oakland, CA (US)

(72) Inventors: Polina V. Lishko, Berkeley, CA (US); Nadja Mannowetz, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 906 days.

(21) Appl. No.: 16/444,992

(22) Filed: Jun. 18, 2019

(65) Prior Publication Data

US 2019/0300565 A1  Oct. 3, 2019

Related U.S. Application Data

(63) Continuation of application No. PCT/US2018/012015, filed on Jan. 2, 2018.

(60) Provisional application No. 62/442,964, filed on Jan. 5, 2017.

(51) Int. Cl.
*A61K 31/56* (2006.01)
*A61K 9/00* (2006.01)
*A61P 15/00* (2006.01)
*A61P 15/18* (2006.01)
*C07J 53/00* (2006.01)

(52) U.S. Cl.
CPC .............. *C07J 53/002* (2013.01); *A61K 9/00* (2013.01); *A61K 9/0034* (2013.01); *A61K 9/0036* (2013.01); *A61K 31/56* (2013.01); *A61P 15/00* (2018.01); *A61P 15/18* (2018.01)

(58) Field of Classification Search
CPC .......... C07J 53/002; A61P 15/18; A61K 9/00; A61K 31/56
See application file for complete search history.

(56) References Cited

U.S. PATENT DOCUMENTS 5,364,879 A    11/1994  Herman
2005/0208147 A1*  9/2005  Vijay ................... A61K 31/704
                                                    424/520

FOREIGN PATENT DOCUMENTS

EP        2698155           2/2014
GB        1456775 A    *  11/1976
WO        2005030790        4/2005
WO        WO-2006081371 A2  *  8/2006  .............. A61P 29/00

OTHER PUBLICATIONS

Mishell et al. ("Contraception by means of a silastic vaginal ring impregnated with medroxyprogesterone acetate," Am. J. Obstet. Gynecol., 1970, 107 (1), 100-107).*
Ramakrishnan et al. ("Controlled release of copper from an intrauterine device using a biodegradable polymer," Contraception, 2015, 92, 585-588).*
Rajasekaran et al. ("Spermicidal Activity of an Antifungal Saponin Obtained from the Tropical Herb *Mollungo pentaphylla*," Contraception, 1993, 47: 401-412).*
ISR-WO; PCT/US18/12015.
Extended EU Search Report; EP 18 735 900.5.
Comm Art 94(3); EP 18 735 900.5.
Gupta RS et al: "Antispermatogenic, antiandrogenic activities of *Albizia lebbeck* (L.) Benth bark extract in male albino rats", Phytomedicine, Elsevier, Amsterdam, NL, vol. 13, No. 4, Mar. 13, 2006 (Mar. 13, 2006), pp. 277-283, XP028022127, ISSN: 0944-7113, DOI: 10.1016/J.PHYMED.2004.11.008.
Shyam S Agrawal et al: "Antifertility activity of methanolic bark extract of *Aegle marmelos* (l.) in male wistar rats", Daru Journal of Pharmaceutical Sciences, Biomed Central Ltd, London, UK, vol. 20, No. 1, Dec. 13, 2012 (Dec. 13, 2012), p. 94, XP021138113, ISSN: 2008-2231, DOI: 10.1186/2008-2231-20-94.
Lishko et al.: "Progesterone activates the principal Ca2+ channel of human sperm", Nature, vol. 471, Mar. 17, 2011 (Mar. 17, 2011), pp. 387-391, XP055518108.
Mannowetz et al., Regulation of the sperm calcium channel CatSper by endogenous steroids and plant triterpenoids, Proceedings of the National Academy of Sciences of the United States of America, vol. 114, No. 22, May 30, 2017 [retrieved on Feb. 6, 2018]. pp. 5743-5748.

* cited by examiner

*Primary Examiner* — Yong S. Chong
(74) *Attorney, Agent, or Firm* — Richard Aron Osman

(57) ABSTRACT

Disclosed are systemic and intravaginal non-hormonal contraceptives comprising a spermicidal triterpenoid. The contraceptive may be in the form of a foam, cream or gel, or in unit form of a pill, vaginal contraceptive film (VCF), suppository, sponge, transdermal or hypodermal patches or a slow release intravaginal device or intrauterine device such as a drug-impregnated silicone elastomer vaginal ring or polymeric IUD.

4 Claims, No Drawings

CONTRACEPTIVE USE OF TRITERPENOIDS

Priority

This application claims priority to PCT/US18/12015, filed: Jan. 2, 2018 and U.S. Ser. No. 62/442,964; filed: Jan. 5, 2017.

This invention was made with government support under Grant Numbers R01GM111802 and R21HD081403 awarded by the National Institutes of Health. The government has certain rights in the invention.

Introduction

In order to succeed in fertilization event, mammalian sperm must penetrate the egg protective shields. This is achieved by sperm enhanced motility mode: the specific drilling motion that is called hyperactivation. The female sex hormone progesterone (P4) that is released from the ovulated egg triggers sperm hyperactivation by activating the calcium influx into sperm tail via the calcium channel of sperm CatSper (1-5) The two steroid hormones progesterone and pregnenolone sulfate (PregS) activate CatSper via a specific signaling mechanism by binding to their receptor on the sperm tail-the enzyme α/β hydrolase domain-containing protein 2 (ABHD2). This means that sperm activation and thus fertilization are dependent on the presence of certain steroid hormones.

As spermatozoa travel through the male and female reproductive tract, they are exposed to a variety of steroid hormones, such as testosterone and estrogen. Rising levels of the steroid hormone cortisol in the body as a result of stress are known to impact fertility (6) by interfering with spermatogenesis and/or sperm functions. Recently, we showed that testosterone, estrogen and cortisol impair CatSper activation by competing with progesterone (7). This indicates that compounds structurally related to the mentioned above steroids may function in the same way by preventing sperm activation. Structurally related to steroid hormones are plant triterpenoids that have been shown to exhibit antifertility properties in mice and rats. The most extensively studied plant triterpenoid with regard to male fertility is lupeol, which is found in mangoes, grapes and olives. It has been shown to possess antifertility properties when orally administered to rats (8). Another plant triterpenoid, pristimerin, which is found in *Tripterygium wilfordii* (also known as "Thunder God Vine") and *Celastrus regelii*, acts as a monoacylglycerol lipase inhibitor, a class of enzymes to which the sperm progesterone receptor ABHD2 belongs. It inhibits the hydrolysis of 2-arachidonoylglyceol (2-AG) to arachidonic acid (AA) and glycerol (9). In sperm 2-AG acts as an endogenous CatSper inhibitor and 2-AG degradation is mediated by ABHD2 in a P4-dependent manner (3). We hypothesized that pristimerin and lupeol can interfere with ABHD2 activity, and explored the ability of these triterpenoids to prevent CatSper activation and thus fertilization.

SUMMARY OF THE INVENTION

The invention provides methods, systems and devices for delivering non-hormonal contraceptive active compounds that comprise naturally occurring and purified or chemically derived terpenoids, as for example an intravaginal contraceptive, orally administrable contraceptive formulation, such as a pill, or an injectable or transdermal contraceptive formulation, particularly in unit dosage and comprising a spermicidal triterpenoid.

Suitable, active terpenoids (e.g. triterpenoids) are readily selected by those skilled in the art according to the disclosed sperm assays, and may be selected or derived from numerous natural, synthetic and engineered sources (10-13).

In embodiments:

the contraceptive is in the form of a pill, patch, microneedle or intravaginal form such as film, foam, cream, or gel, particularly in a predetermined, unit dosage effective for contraception;

the contraceptive is in unit form of a vaginal contraceptive film (VCF), suppository, sponge, or slow release intravaginal devices or intrauterine devices such as drug-impregnated silicone elastomer vaginal rings or polymeric IUDs, and the terpenoid (e.g. triterpenoid) is in a predetermined, unit dosage effective for contraception;

the terpenoid (e.g. triterpenoid) inhibits human sperm hyperactivation induced by either progesterone (P4), pregnenolone sulfate (PregS), or fallopian tube factorinduced activation of the principal human sperm calcium channel, CatSper, such as indicated by influx of calcium currents ($I_{CatSper}$) through the channel measured by electrophysiology and/or calcium imaging;

the terpenoid (e.g. triterpenoid) inhibits P4-, PregS, or fallopian tube factor-induced human sperm hyperactivation or motility;

the triterpenoid is at least one of: a plant triterpenoid, a pentacyclic triterpenoid, a triterpenoid quinone methide or an 11-unsubstituted (11-H) triterpenoid; in particular, we found that position 11-modifications can be detrimental for activity; consistently, RU-486 (mifepristone), and progesterone-11-biotin and progesterone-11-BSA- and all were inactive, whereas progesterone-3-biotin and progesterone-3-BSA were as active as progesterone;

the triterpenoid comprises the ring structure of pristimerin or lupeol, or is a derivative thereof, such as celastrol.

the triterpenoid is selected from pristimerin and lupeol.

In another aspect, the invention provides methods of making and using the subject contraceptives, such as by manufacturing the triterprenoid in a disclosed form, and/or delivering the contraceptive to a vagina, or via the oral delivery route.

In another aspect the invention provides a method of inhibiting sperm motility comprising contacting the sperm with an effective amount of a subject spermicidal triterpenoid, such as in a subject form.

The invention provides reagents and kits for practicing the disclosed methods.

The invention encompasses all combinations of the particular embodiments recited herein, as if each combination had been laboriously recited, such as wherein the triterpenoid is pristimerin or lupeol and the form is a pill, a microneedle, a slow release intravaginal device or intrauterine device such as a drug-impregnated silicone elastomer vaginal ring or polymeric IUD, and the triterpenoid is in a predetermined, unit dosage effective for contraception.

Description of Particular Embodiments and Delivery Methods of the Invention

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Embodiments to deliver active agent(s) include but are not limited to vaginal rings, pills and transdermal patches that release the active agent(s) at a predefined rate.

In embodiments:

the delivery method is in the form of a vaginal ring: A vaginal ring may be a flexible device measuring 20-80 mm in diameter and 240 mm in thickness. The ring may consist of poly(ethylene-co-vinyl acetate), ethylene vinyl acetate copolymer, or silicone elastomer that contains crystals of either pristimerin, lupeol or both. This ring contains sufficient amount of active compound(s) to maintain stable blood concentrations for about 5 weeks releasing between and 100 mcg of active compound(s)/24 hours, but is intended to be used for 3 weeks followed by a ring-free week.

the delivery method is in the form of a pill: The pill may contain sufficient concentrations of active compound(s) (e.g. pristimerin, lupeolor both) to maintain stable blood concentrations by releasing between 1 to 100 mcg of active compound(s)/24 hours. The pill may be used for long-term or on-demand contraception. For long-term contraception, the pill is intended to be used daily for 3 weeks followed by a pill-free week. For on-demand or emergency contraception, the pill is intended to be used daily up to 5 days after vaginal intercourse during the fertile period of the menstrual cycle. Inactive compounds may comprise any combination of dyes, water, corn starch, magnesium stearate, lactose, croscarmellose sodium, polyethylene glycol and titanium dioxide. The purpose of these ingredients is to stabilize the composition of the pill and to assist in dissolving the active compound(s) in the gastrointestinal tract.

The following examples demonstrate that triterpenoids can prevent hormone-induced or fallopian tubal fluid-induced activation of the sperm calcium channel, avert sperm hyperactivation, decrease sperm motility and inhibit sperm fertility.

Plant triterpenoids including pristimerin and lupeol significantly reduce the activation of CatSper by either P4 or PregS. 2-AG hydrolysis by monoacyl lipases, such as ABHD2, is required for CatSper activation. The plant triterpenoid pristimerin was reported to inhibit the activity of related monoacylglycerol lipase (MAGL) (9). If pristimerin can also inhibit ABHD2, then sperm exposure to this compound should prevent CatSper activation by P4 or PregS. To test this hypothesis, human spermatozoa were stimulated with pristimerin, followed by exposure to either a mixture of pristimerin and P4, or to a mixture of pristimerin and PregS. In these experiments we analyzed inward monovalent currents through CatSper ($I_{CatSper}$) of human sperm. Electrophysiology recordings were performed as described in (14). The mere presence of pristimerin did not affect basal $I_{CatSper}$, which indicates that pristimerin did not target the channel directly. However, co-application of pristimerin with P4 or PregS significantly reduced CatSper activation. Compared to stimulation with P4 or PregS alone, the $I_{CatSper}$ stimulation was reduced by 63% (pristimerin and P4) and by 48% (pristimerin and PregS) (7).

Another pharmacologically active plant triterpenoid, which affects sperm functions when orally administered to rats, is lupeol (8). Lupeol is similar in structure to steroid hormones. Comparable to pristimerin, lupeol alone did not affect basal $I_{CatSper}$. However, administration of lupeol with P4 or PregS led to an even stronger inhibition of $I_{CatSper}$ than pristimerin. Compared to CatSper stimulation elicited by P4 or PregS alone, CatSper currents were reduced by 71% and 68%, respectively, in combination with P4 or PregS (7). We have also shown with calcium imaging that pristimerin dose-dependently blocked steroid-activated CatSper activation in human spermatozoa.

Pristimerin and lupeol decrease sperm hyperactivation in the presence of P4. Hyperactivated sperm motility is characterized by a highly asymmetrical bending of the sperm tail due to a CatSper-mediated rise in flagellar calcium concentration (15). Curvilinear velocity (VCL) is the average velocity of the sperm head through the sperm trajectory, which increases during capacitation. A CatSper-mediated calcium rise promotes hyperactivation and makes the sperm trajectory less linear, which results in an increase of VCL. Capacitation increases CatSper activity, which results in a higher percentage of sperm with hyperactivated motility. Thus, capacitated spermatozoa tend to have higher VCL values than non-capacitated. Since both P4 and PregS activate CatSper, while pristimerin and lupeol inhibit it, we explored whether VCL values of human sperm are affected in the presence of plant triterpenoids or steroid hormones. As expected, neither of the compounds changed VCL values of non-capacitated sperm cells. In capacitated spermatozoa, P4 stimulation increased VCL by 12%, comparable to numbers reported by others (3, 16), but VCL values remained unchanged in the presence of PregS, pristimerin or lupeol alone (7). When spermatozoa were stimulated with P4+pristimerin or P4+lupeol, VCL values were reduced by 39% and 48%, respectively, in comparison to VCL values obtained in the presence of P4, and the reduced VCL values were comparable to those of non-capacitated cells. Stimulating capacitated sperm with PregS in combination with pristimerin or lupeol decreased VCL by 18% and 9%, respectively, compared to sperm, which were treated with PregS alone. VCL values of non-capacitated sperm remained unchanged under such conditions. Since CatSper is not only required for hyperactivation but also for basal motility, we sought to determine whether pristimerin and lupeol also affect sperm motility. The number of both capacitated and non-capacitated motile spermatozoa remained unchanged when stimulated with either compounds. However, when P4 was co-applied with pristimerin or lupeol the percentage of motile capacitated sperm decreased significantly by 19%, respectively, whereas the values of non-capacitated cells did not change. Co-stimulation with PregS and pristimerin or lupeol, however, did not result in a significant reduction of motile capacitated or non-capacitated sperm. These results indicate that triterpenoids like pristimerin and lupeol have the capacity to significantly reduce sperm hyperactivation by blocking the P4-mediated activation of CatSper.

Intravaginal Spermicidal Triterpenoid Formulations

Formulations encompass a representative spermicidal triterpenoid, including pristimerin, lupeol or both compounds (e.g. 50:50 w/w combinations).

A) Intravaginal spermicidal triterpenoid aerosol foam (canister with applicator); active ingredient: spermicidal triterpenoid, 10% inactive ingredients: benzoic acid, cellulose gum, acetyl alcohol, fragrance, glacial acetic acid, methylparaben, phosphoric acid, polyvinyl alcohol, propellant A-31, propylene glycol, purified water, sorbic acid, stearamidoethyl diethyl amine, stearic acid.

B) Intravaginal spermicidal triterpenoid gel (prefilled applicators, 0.1 oz (2.6 g) each; active ingredients: spermicidal triterpenoid, 5%; inactive ingredients: lactic acid, methylparaben, povidone, propylene glycol, water (purified), sodium carboxy methyl cellulose, sorbic acid, sorbitol C) Vaginal spermicidal triterpenoid contraceptive sponge; active ingredients: in each sponge: spermicidal triterpenoid (1000 mg); inactive ingredients: benzoic acid, citric acid, sodium dihydrogen citrate, sodium metabisulfite, sorbic acid, water in a polyurethane foam sponge.

D) Vaginal spermicidal triterpenoid contraceptive film; active ingredient: spermicidal triterpenoid (30%); inactive ingredients: glycerin, polyvinyl alcohol, purified water.

REFERENCES

1. Brenker C, et al. (2012) The CatSper channel: a polymodal chemosensor in human sperm. *The EMBO journal* 31(7):1654-1665.
2. Lishko P V, Botchkina I L, & Kirichok Y (2011) Progesterone activates the principal Ca2+channel of human sperm. *Nature* 471(7338):387-391.
3. Miller M R, et al. (2016) Unconventional endocannabinoid signaling governs sperm activation via the sex hormone progesterone. *Science* 352(6285):555-559.
4. Smith J F, et al. (2013) Disruption of the principal, progesterone-activated sperm Ca2+channel in a CatSper2-deficient infertile patient. *Proceedings of the National Academy of Sciences of the United States of America* 110(17):6823-6828.
5. Strunker T, et al. (2011) The CatSper channel mediates progesterone-induced Ca2+influx in human sperm. *Nature* 471(7338):382-386.
6. Whirledge S & Cidlowski J A (2010) Glucocorticoids, stress, and fertility. *Minerva endocrinologica* 35(2):109-125.
7. Mannowetz N, Miller M R, & Lishko P V (2017) Regulation of the sperm calcium channel CatSper by endogenous steroids and plant triterpenoids. *Proceedings of the National Academy of Sciences of the United States of America*.
8. Gupta R S, et al. (2005) Induction of antifertility with lupeol acetate in male albino rats. *Pharmacology* 75(2): 57-62.
9. King A R, et al. (2009) Discovery of potent and reversible monoacylglycerol lipase inhibitors. *Chemistry & biology* 16(10):1045-1052.
10. Lu X, Tang K, & Li P (2016) Plant Metabolic Engineering Strategies for the Production of Pharmaceutical Terpenoids. *Front Plant Sci* 7:1647.
11. Moses T, Pollier J, Thevelein J M, & Goossens A (2013) Bioengineering of plant (tri)terpenoids: from metabolic engineering of plants to synthetic biology in vivo and in vitro. *New Phytol* 200(1):27-43.
12. Sawai S & Saito K (2011) Triterpenoid biosynthesis and engineering in plants. *Front Plant Sci* 2:25.
13. Tholl D (2015) Biosynthesis and biological functions of terpenoids in plants. *Adv Biochem Eng Biotechnol* 148: 63-106.
14. Lishko P, Clapham D E, Navarro B, & Kirichok Y (2013) Sperm patch-clamp. *Methods in enzymology* 525:59-83.
15. Suarez S S (2008) Control of hyperactivation in sperm. *Human reproduction update* 14(6):647-657.
16. Calogero A E, et al. (1996) Effects of gamma-aminobutyric acid on human sperm motility and hyperactivation. *Molecular human reproduction* 2(10):733-738.

The invention claimed is:

1. A pharmaceutical composition comprising a polymeric intrauterine device (IUD) impregnated with a spermicidal triterpenoid in a predetermined dosage effective for human contraception, wherein the triterpenoid is selected from the group consisting of pristimerin, celastrol and lupeol.

2. The composition of claim 1, wherein the triterpenoid is pristimerin.

3. The composition of claim 1, wherein the triterpenoid is celastrol.

4. The composition of claim 1, wherein the triterpenoid is lupeol.

* * * * *